United States Patent [19]
Yamamoto et al.

[11] Patent Number: 5,989,022
[45] Date of Patent: Nov. 23, 1999

[54] SHADE MATCHING DEVICE FOR ARTIFICIAL TEETH AND CROWN RESTORATION

[75] Inventors: Makoto Yamamoto, Osaka; Yukuo Kuze, Kyoto, both of Japan

[73] Assignee: Kabushiki Kaisha Shofu, Kyoto-fu, Japan

[21] Appl. No.: 08/948,317

[22] Filed: Oct. 10, 1997

[30] Foreign Application Priority Data

Oct. 14, 1996 [JP] Japan ..................................... 8-010255

[51] Int. Cl.⁶ .................................................. A61C 19/10
[52] U.S. Cl. ........................................................ 433/26
[58] Field of Search ................................. 433/26; 206/83

[56] References Cited

U.S. PATENT DOCUMENTS 2,846,725  8/1958  Tryfus ........................................ 433/26
3,436,156  4/1969  Adler et al. ............................... 433/26
5,066,227  11/1991  Pozzi ......................................... 433/26

OTHER PUBLICATIONS

Metal Ceramics by Makoto Yamamoto, published in 1985, pp. 230–231.

*Primary Examiner*—John J. Wilson
*Attorney, Agent, or Firm*—Stevens, Davis, Miller & Mosher, L.L.P.

[57] ABSTRACT

The present invention provides a shade matching device for an artificial teeth and a crown restoration in order to correctly adjust the artificial teeth to the natural teeth in shade, which comprises a set of:
  shade guides, and
  a gingival colored holder which has concaves shaped fitting a neck part of an artificial teeth or a crown restoration and retainers into which the stick of the shade guide can be inserted.

2 Claims, 1 Drawing Sheet

SHADE MATCHING DEVICE FOR ARTIFICIAL TEETH AND CROWN RESTORATION

BACKGROUND OF THE INVENTION

The present invention relates to a shade matching system for selecting the shade of an artificial teeth and crown restoration.

According to a conventional method a shade guide with a stick for an artificial teeth and crown restoration (simply referred to as a "shade guide" hereinafter) has been used alone or used while the stick of the shade guide was inserted into a holder. This embodiment is adopted for the sake of preventing damage at selling or transportation. According to this conventional method mismatching in shade between the natural tooth and the artificial teeth which was actually fixed in a mouth has been often caused owing to a large error generated when the shade was examined by shade guides in the mouth of a patient.

Conventional holders are liable to cause mismatching in the shade because of difficulty of adjusting the shade due to contrast effect of color caused by the color reflection of the background or the stick when shade of the teeth is examined in patient's mouth, when there is a space between adjacent shade guides or between the shade guides and the holder. Particularly, if there is a space at the neck of teeth, it was difficult to determine a correct shade due to the contrast effect of shade by the influence of color of the background and the stick when comparing the shade guide with natural teeth which is in contact with the gingiva.

SUMMARY OF THE INVENTION

According to the present invention the holder is colored gingival color. It is also designed to minimize the mismatch in the shade between the natural teeth and the artificial teeth or crown restoration, in such a way that the shade of finished crown or artificial teeth is adjusted with that of patient's mouth before setting, on a condition that the shade guide's tabs are in contact with the holder.

DETAILED DESCRIPTION OF THE INVENTION

The present invention relates to a shade matching device for an artificial teeth or a crown restoration which comprises a set of:
- shade guides with a stick for an artificial teeth or crown restoration (simply referred to as "shade guide" in the present specification), and
- a gingival colored holder which has concaved shape fitting to a neck part of an artificial teeth or teeth crown restoration with the retainers into which the stick of the shade guide can be fixed.

The term "crown restoration" in the present specification includes restorative materials for dental decay, partial deficit of teeth and the like.

The holder may be shaped even or uneven, but preferably uneven as simulating gingival shape. The mismatching caused by the contrast effect of color can be decreased thereby. The holder is preferably prepared with rubber elastomers which has gingival color and simulating the state of the gingival surface or is preferably provided with concaved shape, with which shade tabs are tightly in contact. The neck of the artificial teeth or that of shade guides is preferably fitted to be slightly embedded near the concaves, by which the natural appearance is enhanced and the mismatching will be decreased.

The holder part of the present invention may be preferably made of a synthetic resins such as hard vinyl chloride resins, styrene resins, acrylic resins, and the like or rubber like elastomers such as soft vinyl chloride resins, urethane resins, silicone resins, styrene-butadiene copolymers and the like, which is colored gingival color. Further, it is possible to simulate the natural appearance of the neck part by substituting the above synthetic resins with rubber elastomers such as soft vinyl chlorides, urethane resins, silicone resins, styrene-butadiene copolymers and the like around the concaves and by fitting these elastomers as the neck part is slightly embedded by the elastomers. Further, the holder is furnished with concaves fitting the shape of neck part of the shade guides, and retainers into which the stick of the shade guides can be inserted. The retainers may be furnished with projections for slides or fabricated to a shape so that the shade guides can be fastened attachably or removably. The retainers are preferably furnished in the corresponding number of the shade guides, and can lightly fasten the shade guides. Accordingly, the retainers may not necessarily have projections, but they may have any lightly fastening mechanism.

The holder may have windows in order to confirm the color code of the shade guides, when they are inserted into the retainers, without the removal of the shade guide.

The number of concaves may be one or more, preferably 3 to 5 for comparing and selecting the shade of the artificial teeth. The artificial teeth may be slightly contacted with or away from the neighboring tooth 1 to 5 mm. Preferably to be slightly in contact with neighboring tooth.

COMPARATIVE EXAMPLE

Figure 1:
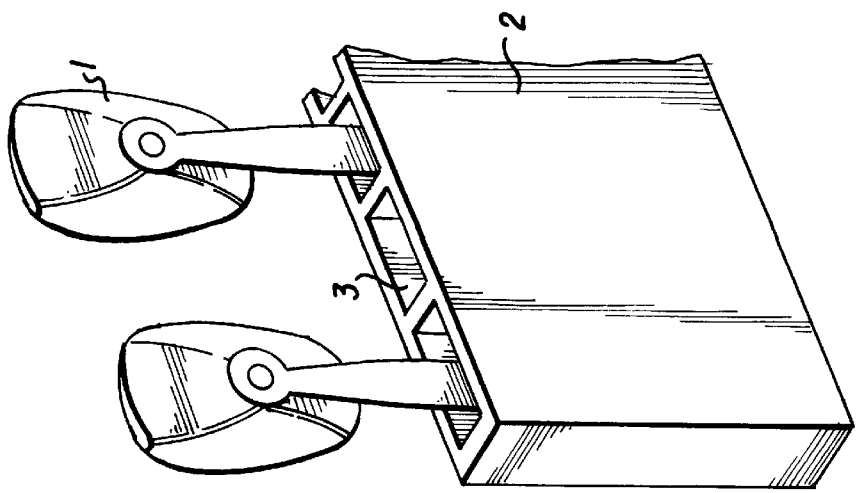
FIG. 1 illustrates a perspective view of a conventional shade guide.

One of embodiment of a conventional holder is illustrated by FIG. 1. The shade guides (1) are inserted into slots (3) of the holder (2) made of plastic or metal to be fastened. The holder having a shape of rectangle, fan-shaped, circle and the like has been sold.

EXAMPLE

Figure 3:
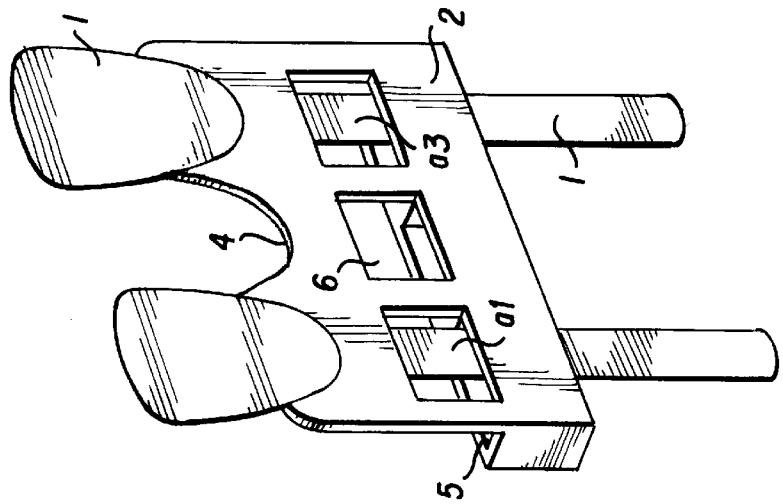
FIG. 3 illustrates a perspective view of a shade matching device of the present invention (frontside).
Figure 2:
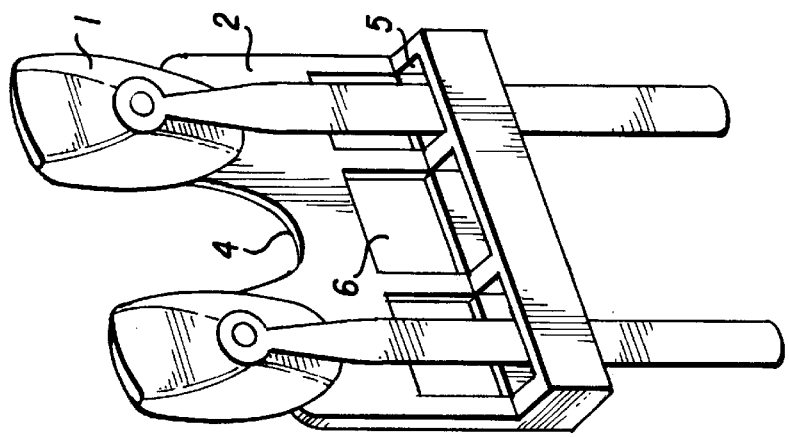
FIG. 2 illustrates a perspective view of a shade matching device of the present invention (backside).

FIGS. 2 and 3 illustrate the embodiments of a shade matching device for artificial teeth and crown restoration of the present invention, in which a holder is gingival colored, and has one or more concaves (4) so as to be fitted with the necks part, and retainers (5) can hold the stick of shade guides for an artificial teeth, so that the neck part can be fitted by the concaves (4) when the stick of the shade guides are inserted into the retainers (5). The window (6) may be furnished at the center of the holder as illustrated in FIGS. 2 and 3.

In these examples three artificial teeth or shade guides can be inserted and removed, but the numbers thereof are not restrictive. One or more artificial tooth or shade guides may be used but 3 to 5 are most preferable for comparing the shade. Shade matching can be processed in an optimal way by arranging the shade guide tabs in the same order as that of artificial teeth fitted into the mouth, such as central incisor, lateral incisor and canine.

Using the shade matching device of the present invention the shade of the artificial teeth or crown restoration can be easily matched with shade of natural tooth in a mouth. When the device was made of synthetic resins, it can be inserted without any problems which are often caused by slight differences in the size, shape in left and right and the like of the artificial tooth. Particularly, when the concaves are made of rubber elastomers, the system can be used without any problems because the slight difference in the shape is absorbed by the elastomers.

What is claimed is:

1. A shade matching device for at least one artificial tooth and crown restoration, which comprises a set of:

shade guides with a stick having an artificial tooth attached thereto, wherein said artificial tooth attached to said stick has a neck portion, and a gingival colored holder which has concave shapes corresponding to the neck shape of the portion of said artificial tooth, wherein the shade guides are removably mounted in said holder such that the labial portion of the neck is fitted against the gingival colored holder whereby the color of the gingival color of the holder influences the color perception of the artificial tooth to simulate the tooth in a mouth, and retainers in which the stick of the shade guide can be inserted.

2. A shade matching device for at least one artificial tooth and crown restoration of claim 1, in which the holder comprises windows for confirming a color code of the shade guide.

* * * * *